US006375992B1

(12) United States Patent
Blumenstein-Stahl et al.

(10) Patent No.: US 6,375,992 B1
(45) Date of Patent: Apr. 23, 2002

(54) METHODS OF HYDRATING MAMMALIAN SKIN COMPRISING ORAL ADMINISTRATION OF A DEFINED COMPOSITION

(75) Inventors: Gabriele Blumenstein-Stahl, Hofheim; Ute Podbielski, Hofheim am Taunus; Christa-Marie Fischer, Eschborn, all of (DE)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/510,800

(22) Filed: Feb. 23, 2000

(51) Int. Cl.$^7$ .................. A61K 35/78; A61K 39/385

(52) U.S. Cl. .................. 424/729; 424/725; 424/744; 424/766

(58) Field of Search .................. 424/195.1, 725, 424/729, 766, 744; 426/601, 597, 648, 427

(56) References Cited

U.S. PATENT DOCUMENTS

| | | | |
|---|---|---|---|
| 4,574,085 A | 3/1986 | Dolkart et al. | |
| 5,147,650 A | 9/1992 | Fregly et al. | |
| 5,378,465 A | 1/1995 | Zeines | 424/195.1 |
| 5,403,921 A | 4/1995 | Montner et al. | |
| 5,468,737 A | 11/1995 | McAnalley et al. | |
| 5,567,424 A | 10/1996 | Hastings | |
| 5,681,569 A | 10/1997 | Kuznicki et al. | |
| 5,869,540 A | 2/1999 | Smith | 514/783 |
| 5,916,573 A | 6/1999 | Spiers et al. | 424/401 |
| 5,925,348 A | 7/1999 | Riley et al. | 424/94.5 |
| 5,939,395 A | * 8/1999 | Yu et al. | |

FOREIGN PATENT DOCUMENTS

| | | | |
|---|---|---|---|
| HU | 38042 T | * 4/1986 | |
| JP | 96038122 | 2/1996 | |
| JP | 96298935 | 11/1996 | |
| JP | 97009904 | 1/1997 | |
| WO | WO 94/22322 | 10/1994 | |
| WO | WO 97/32947 | 9/1997 | |
| WO | WO 99/48386 | 9/1999 | A23L/1/30 |

OTHER PUBLICATIONS

"Anti–Inflammatory and Wound Healing Properties of Aloe Vera", Fitoterapia, Volume LXV, No. 2, 1994.
L. Pressnell, *Beyond Refreshment*; Soft Drinks International; Feb. 1998; pp. 24–25.
Peter Wasko; *Just What the Doctor Ordered*; Beverage Industry; Aug. 1996; vol. 87 No. 8; p. 29.
*Turning Japanese*; Packaging Week; Sep. 19, 1996; p. 25.
David Jago; *Herbs and Health*; International Food Ingredients; Mar.–Apr. 1999, vol. 2, pp. 40–41.
Chapin Clark; *In Your Face*; Supermarket News; Mar. 1, 1999; pp. 37–38.
*People's Choice Ocean Mineral Drink*; Marketing Intelligence Service, Ltd.; Product Alert; Oct. 12, 1998.
*Lily Of The Desert Organic Aloe Vera Drinks*; Marketing Intelligence Service, Ltd.; Product Alert; Aug. 8, 1999.
*Soft Drink Report*, Beverage Industry; Mar., 1998; pp. 44–47.
M. Fenech, et al.; *Moderate Wine Consumption Protects Against Hydrogen Peroxide–Induced DNA Damage*; Mutagenesis, vol. 12, No. 4, pp. 289–296, 1997.
J. L. Bolognia, I. M. Braverman, M. E. Rousseau, P. M. Sarrel; *Skin Changes in Menopause*; Maturitas, 11 (1989) 295–304.
Albert M. Kligman, M. D., PhD.; *Perspectives And Problems in Cutaneous Gerontology*; vol. 73, No. 1, Jul. 1979; pp. 39–45.
J. Wepierre, J. P. Marty; Percutaneous Absorption And Lipids in Elderly Skin; J. Appl. Cosmetol. 6, 79–92 (Apr.–Jun. 1988).
C. Escoffier, et al.; *Age–Related Mechanical Properties Of Human Skin: An In Vivo Study*; Journal Of Investigative Dermatology; vol. 93, No. 3 Sep. 1989; pp. 353–357.
Barbara A. Gilchrest, M. D.; *Age–Associated Changes In The Skin*; Journal Of The American Geriatrics Society; vol. 30, No. 2; Feb., 1982, pp. 139–143.
Jean L. Bolognia, M. D.; *Aging Skin*; The American Journal Of Medicine; vol. 98 (suppl 1A); Jan. 16, 1995; pp. 1A–99S–1A–103S.
E. Berardesca et al.; *In Vivo Hydration And Water–Retention Capacity Of Stratum Corneum In Clinically Uninvolved Skin In Atopic And Psoriatic Patients*; Acta Derm Venereol (Stockh) 1990; 70:400–404.
D. Grindlay & T. Reynolds; *The Aloe Vera Phenomenon: A Review Of The Properties and Modern Uses Of The Leaf Parenchyma Gel*; Journal Of Ethnopharmacology, 16 (1986) 117–151.

(List continued on next page.)

Primary Examiner—Christopher R. Tate
Assistant Examiner—Michele C. Flood
(74) *Attorney, Agent, or Firm*—Kelly L. McDow-Dunham; Carl J. Roof

(57) ABSTRACT

The present invention is directed to methods of hydrating mammalian skin comprising orally administering a substantially decaffeinated composition comprising one or more flavanols, preferably through the presence of green tea solids. The present invention is further directed to kits comprising a substantially decaffeinated composition comprising one or more flavanols and information that oral administration of the composition provides one or more skin health benefits, particularly hydration of mammalian skin. Particularly preferred compositions suitable for oral administration comprise:

a) aloe;
b) glycerol;
c) a further component comprising one or more flavanols; and
d) at least about 50% water.

Other particularly preferred embodiments which provide hydration of mammalian skin are described herein.

17 Claims, No Drawings

OTHER PUBLICATIONS

S. P. Joshi; *Chemical Constituents And Biological Activity Of Aloe Barbadensis–A Review*; Journal Of Medicinal And Aromatic Plant Sciences; 20; (1998) 768–773.

J. E. O'Connell, P. F. Fox; *Effect Of Extracts Of Oak (Quercus Petraea) Bark, Oak Leaves, Aloe Vera (Curacao Aloe), Coconut Shell And Wine On The Colloidal Stability Of Milk And Concentrated Milk*; Food Chemistry; 66; (1999) 93–96.

F. Capasso, et al.; *Aloe And Its Therapeutic Use*; Phytotherapy Research, vol. 12, S124–S127 (1998).

Ronald M. Shelton; *Aloe Vera—Its Chemical And Therapeutic Properties*; International Journal Of Dermatology; Oct., 1991; C 30 (10); 679–683.

*Beverages: Pokka Corp. Markets Three New Beverages*; Comline–Consumer Goods p990203100031; Feb. 3, 1999.

W. Montagna, K. Carlisle; *Structural Changes in Ageing Skin*; British Journal Of Dermatology (1990) 122, Supplement 35, 61–70.

G. W. Marshall, Jr. et al.; *Effect Of Citric Acid Concentration On Dentin Demineralization, Dehydration, And Rehydration: Atomic Force Microscopy Study*; 1998 John Wiley & Sons, Inc.; pp. 500–507.

M. E. Beridot–Therond, et al.; *Short Term Effects Of The Flavour Of Drinks On Ingestive Behaviours In Man*; Appetite, 1998. 31 67–81, Article No. ap970153.

M. Gniadecka, et al.; *Water And Protein Structure In Photoaged And Chronically Aged Skin*; The Journal Of Investigative Dermatology; vol. III, No. 6; Dec. 1998.

Sun H. Kim, et al.; *Carbonated Beverage Consumption And Bone Mineral Density Among Older Women; The Rancho Bernardo Story*; American Journal Of Public Health, Feb. 1997, vol. 87, No. 2.

M. Santosham, M. D., et al.; *A Double–Blind Clinical Trial Comparing World Health Organization Oral Rehydration Solution With A Reduced Osmalarity Solution Containing Equal Amounts Of Sodium And Glucose*; The Journal Of Pediatrics, Jan. 1996; pp. 45–51.

P. Quinlan, et al.; *Effects Of Hot Tea, Coffee, And Water Ingestion On Physiological Responses And Mood: The Role Of Caffeine, Water And Beverage Type*; Psychophamracology (1997) 134:164–173.

James D. Lane; *Effects Of Brief Caffeinated–Beverage Deprivation On Mood, Symptoms, And Psychomotor Performance*; Pharmacology Biochemistry And Behavior, vol. 58, No. 1, pp. 203–208, 1997

I. Hindmarch, et al.; *The Effects Of Black Tea And Other Beverages On Aspects Of Cognition And Psychomotor Performance*; Psychopharmacology (1998) 139:230–238.

Boguslaw, et al.; *Effect Of Drink Flavor And NaCl On Voluntary Drinking And Hydration In Boys Exercising In The Heat*; The American Physiological Society, 1996; pp. 1112–1117.

Gisolfi, et al.; *Effect Of Beverage Osmolality On Intestinal Fluid Absorption During Exercise*; The American Physiological Society, 1998; pp. 1941–1948.

P. A. O'Neill, et al.; *Response To Dehydration In Elderly Patients In Long–term Care*; Aging Clin. Exp. Res., vol. 9, No. 5, pp. 372–377; 1997.

R. J. Maughan & S. M. Shirreffs; *Recovery From Prolonged Exercise; Restoration Of Water And Electyrolyte Balance*; Journal Of Sports Sciences, 1997, 15, 297–303.

Ronald T. Verrillo, et al.; *Effects Of Hydration On Tactile Sensation*; Somatosensory & Motor Research, 1998; 15(2); 93–108.

E. M. R. Kovacs, et al.; *Urine Color, Osmolality And Specific Electrical Conductance Are Not Accurate Measures Of Hydration Status During Postexercise Rehydration*; The Journal Of Sports Medicine And Physical Fitness; vol. 39; No. 1; pp. 47–53.

G. Yosipovitch, et al.; *Time–Dependent Variations of the Skin Barrier Function in Humans: Transperidermal Water Loss, Stratus Corneum Hydration, Skin Surface pH, and Skin Temperature*; The Journal Of Investigative Dermatology; vol. 110; No. 1; Jan., 1998; pp. 20–23.

Dale R. Wagner, Ph.D; *Hyperhydrating With Glycerol: Implications For Athletic Performance*; Journal Of The American Dietetic Association; Feb. 1999; vol. 99; No. 2; pp. 207–212.

Robert A. Robergs & Sharon E. Griffin; *Glycerol Biochemistry, Pharmacokinetics and Clinical and Practical Applications*; Sports Med; Sep. 1998; 26 (3).

* cited by examiner

METHODS OF HYDRATING MAMMALIAN SKIN COMPRISING ORAL ADMINISTRATION OF A DEFINED COMPOSITION

FIELD OF THE INVENTION

The present invention is directed to compositions which are suitable for oral administration, and kits and methods thereof useful for hydrating mammalian skin. The compositions are preferably food or beverage compositions, preferably beverage compositions.

BACKGROUND OF THE INVENTION

The cosmetic industry is replete with lotions, creams, gels, and other formulations which are intended for improving the appearance of human skin. Typically, such formulations are directed to alleviating flaky and dry skin conditions. Most recently, there has been a trend toward marketing such cosmetic formulations for improving the appearance of, or reducing, fine lines and wrinkles, particularly on the face and hands of the user. However, the beneficial effects of these formulations may not be achieved wherein the user consumes dehydrating foods and beverages, for example those containing significant amounts of caffeine or salt. Additionally, realization of the beneficial effects of these formulations depends upon continual application of the formulations to the affected areas, which translates into increased inconvenience and significant expense for the user.

Accordingly, it would be highly beneficial to provide a composition which hydrates mammalian skin from within, for example, as an integral factor of the user's diet. Unfortunately, however, there is limited information in the art regarding how to achieve such hydration from within and, correspondingly, limited availability of optimized products which deliver hydration to the user together with information that such products will deliver a skin hydrating effect.

Kuznicki et al., U.S. Pat. No. 5,681,569, issued Oct. 28, 1997, discloses use of a flavanol and various other ingredients to provide cellular hydration and water distribution in the body, for example, as needed by athletes experiencing rapid dehydration. It is further disclosed that such ingredients speed the absorption of water in the body, after rapid water loss. However, Kuznicki et al. does not recognize a need for hydration of mammalian skin even in the absence of strenuous activity, and particularly does not recognize any hydration benefit as extended to mammalian skin hydration.

Excitingly and surprisingly, the present inventors have discovered that use of the defined compositions described herein provide a mammalian skin benefit which can be measured by analytical techniques. The defined compositions herein comprise one or more flavanols, preferably through the presence of green tea and/or red grape extract, and may additionally comprise glycerol and/or aloe to further enhance the skin hydrating effect. It is the discovery of the present inventors that use of such flavanols provides this hydrating benefit, which translates into alleviation of dry and flaky skin, and even the improvement of fine lines and wrinkles. Thus, provided herein are compositions, kits, and methods specifically designed to achieve mammalian skin hydration.

SUMMARY OF THE INVENTION

The present invention is directed to methods of hydrating mammalian skin comprising orally administering a composition comprising one or more flavanols, most preferably through the presence of green tea solids. The present invention is further directed to kits comprising a composition comprising one or more flavanols and information that oral administration of the composition provides one or more skin health benefits, particularly hydration of mammalian skin. Preferably, the compositions herein are substantially decaffeinated. Particularly preferred compositions suitable for oral administration comprise:

a) aloe;
b) glycerol;
c) a further component comprising one or more flavanols; and
d) at least about 50% water.

DETAILED DESCRIPTION OF THE INVENTION

The present invention is directed to compositions which are suitable for oral administration, and kits and methods thereof useful for hydrating mammalian skin. The kits comprise a composition as described herein and information that use of such kit provides one or more skin health benefits. The compositions are preferably food or beverage compositions, most preferably beverage compositions.

Publications and patents are referred to throughout this disclosure. All references cited herein are hereby incorporated by reference.

All percentages and ratios are calculated by weight unless otherwise indicated. All percentages and ratios are calculated based on the total composition unless otherwise indicated.

All component, ingredient, composition levels, or the like, are in reference to the active level of that component or composition, and are exclusive of impurities, for example, residual solvents or by-products, which may be present in commercially available sources.

Referred to herein are trade names for components including, but not limited to, certain teas, aloes, and other components. The inventor herein does not intend to be limited by materials under a certain trade name. Equivalent materials (e.g., those obtained from a different source under a different name or catalog (reference) number) to those referenced by trade name may be substituted and utilized in the compositions, kits, and methods herein.

In the description of the invention various embodiments and/or individual elements are disclosed. As will be apparent to the ordinarily skilled practitioner, all combinations of such embodiments and elements are possible and can result in preferred executions of the present invention.

The compositions, methods, and kits herein may comprise, consist essentially of, or consist of any of the elements as described herein.

Compositions of the Present Invention

It has been surprisingly discovered by the present inventors that one or more flavanols, when orally administered in a present composition, provides skin health benefits including hydration of mammalian skin. Preferably, a component selected from substantially decaffeinated tea solids (most preferably, green tea), red grape extract, or both, provides the flavanols in the composition. In a particularly preferred embodiment herein this benefit is further advanced wherein one or both components selected from aloe and glycerol, preferably glycerol, are further included within the compositions. Accordingly, the present inventors describe herein compositions containing at least one or more flavanols, and optionally one or more of aloe, glycerol, and other preferred components. Each of these components are more particularly described herein below.

In the most preferred embodiments of the present invention, the compositions herein comprise one or more flavanols, preferably wherein the presence of the flavanols is due to the presence of a tea solid in the composition (most preferably, green tea solids) and/or red grape extract. A particularly preferred embodiment of this type includes beverage compositions comprising green tea solids, glycerol, and optionally red grape extract and/or aloe, and at least about 50% water. Another particularly preferred embodiment of this type includes beverage compositions comprising green tea solids, aloe, glycerol, and red grape extract, and at least about 50% water. Further optional elements of beverage compositions, even more preferred levels of water, and preferred ranges and embodiments of the tea solids, aloe, glycerol, and red grape extract are defined further herein below. For example, the beverage compositions most preferably further comprise a beverage component selected from fruit juice, milk solids, fruit flavors, botanical flavors, and mixtures thereof, as is further described herein.

The compositions herein may be caffeinated or substantially decaffeinated, and are preferably substantially decaffeinated such to avoid counteracting the skin hydrating effect herein. As used herein, "substantially decaffeinated", with respect to the composition, means that the composition comprises less than about 0.5% caffeine, preferably less than about 0.25% caffeine, more preferably less than about 0.1% caffeine, even more preferably less than about 0.05% caffeine, and most preferably less than about 0.005% caffeine, by weight of the composition.

Flavanols

The compositions herein, which may optionally be included in the present kits or utilized in the present methods, comprise at least one flavanol. As used herein, the term "flavanol" means catechins (including gallocatechins), epicatechins (including epigallocatechins, epigallocatechingallates, and epicatechingallates), anthocyanins, procyanidins (oligomers of catechins), tannins (polymers of catechins), and their derivatives. Preferably, "flavanol" means catechins (including gallocatechins), epicatechins (including epigallocatechins, epigallocatechingallates, and epicatechingallates) and anthocyanins. These derivatives include the sugar salts, sugar esters, and other physiologically acceptable derivatives.

The present inventors have discovered that the mammalian skin hydrating effect herein is optimized wherein from about 0.0001% to about 1% of total flavanols, more preferably from about 0.001% to about 0.5% of total flavanols, still more preferably from about 0.002% to about 0.35% of total flavanols, even more preferably from about 0.0025% to about 0.1% of total flavanols, and most preferably from about 0.003% to about 0.075% of total flavanols is included within a composition, all by weight of the composition.

Flavanols are well-known compounds which are largely present in fruits, vegetables, and tea solids, and may be extracted from these natural sources using any method known to those skilled in the art. Preferably, the flavanols herein are present in the compositions herein through the presence of one or more tea solids and/or red grape extract.

Among the most important flavanols for use herein are catechin, epicatechin, gallocatechin, epigallocatechin, epicatechingallate, and epigallocatechingallate. These catechins are commercially available. For example, many of these catechins are available from Sigma-Aldrich Co., St. Louis, Mo.

Other important flavanols for use herein are anthocyanins. Anthocyanins are also commercially available and are particularly abundant in red grape extract, as is set forth further below.

Therefore, the preferred sources of flavanols in the present invention are tea solids (preferably, green tea) and red grape extract, most preferably green tea.

The green tea (or other teas) may be provided in the form of a tea extract. The tea extract may be obtained from the extraction of unfermented teas, fermented teas, partially fermented teas, and mixtures thereof. Preferably, the tea extracts are obtained from the extraction of unfermented and partially fermented teas. Both hot and cold extracts may be utilized herein. Suitable methods for obtaining tea extracts are well known. See e.g., Tsai, U.S. Pat. No. 4,935,256, issued June 1990; Lunder, U.S. Pat. No. 4,680,193, issued July 1987; and Creswick, U.S. Pat. No. 4,668,525, issued May 26, 1987. As used herein, unless otherwise provided, "tea" means the tea solid itself or an extract thereof containing one or more flavanols. For example, "green tea" means the green tea solid itself or an extract thereof containing one or more flavanols.

Preferably, the flavanol herein is present in one or more tea solids and is used in the present compositions by including such tea solid in the composition, or by extracting the flavanol from such tea solid. As used herein, "tea solids" refers to solids obtained from the genus Camellia including *Camellia sinensis* and *Camellia assaimica*, and the genus Phyllanthus including *Catechu gambir*, or the Uncaria family of tea plants, for example, freshly gathered tea leaves, fresh tea leaves which are dried immediately after gathering, fresh tea leaves that have been heat-treated before drying to inactivate any enzymes present, unfermented tea, fermented tea, instant green fermented tea, partially fermented tea leaves and aqueous extracts of these leaves. Preferably, the flavanols are present in *Camellia sinensis* (i.e., green tea). Thus, in a most preferred embodiment herein, the flavanol(s) included with a composition herein is present in green tea solids and is used in the present compositions by including green tea in the composition, or by extracting the flavanol(s) from green tea.

Tea solids for use in compositions of the present invention can be obtained by known and conventional tea solid extraction methods. A particularly preferred source of green tea solids can be obtained by the method described in Ekanavake et al., U.S. application Ser. No. 08/606,907, filed Feb. 26, 1996. Tea solids so obtained will typically comprise caffeine (as set forth below, such caffeine should be substantially removed to achieve the benefits of the present invention), theobromine, proteins, amino acids, minerals and carbohydrates. Suitable beverages containing tea solids can be formulated according to Tsai et al., U.S. Pat. 4,946, 701, issued Aug. 7, 1990. See also, Ekanayake et al., U.S. Pat. No. 5,427,806, issued Jun. 26, 1995, for a suitable sources of green tea solids for use in the present invention.

Extraction of one or more flavanols from a natural material, including tea solids, is well-known to one of ordinary skill in the art. For example, extraction with ethyl acetate or a chlorinated solvent may be used. Additionally, flavanols may be prepared by synthetic or other appropriate chemical methods.

The tea solids and the compositions including the tea solid should be substantially decaffeinated to avoid a dehydrating effect. As used herein, "substantially decaffeinated", with respect to the tea material, means that the tea material comprises less than about 0.5% caffeine, preferably less than about 0.25% caffeine, more preferably less than about 0.1% caffeine, even more preferably less than about 0.05% caffeine, and most preferably less than about 0.005% caffeine, by weight of the tea solid.

Also preferably, the flavanol herein is present in red grape extract and is used in the present compositions by including such red grape extract in the composition, or by extracting the flavanol from such extract. Again, the present inventors have excitingly discovered the mammalian skin hydrating effect resulting from the flavanol(s) present in red grape extract, including the catechins, tannins, and primarily the anthocyanins. The red grape extract may contain other important compounds for enhancing total health, including skin health, such as phenolic acids. Preferably, the red grape extract contains at least about 1%, more preferably at least about 5%, and most preferably at least about 9% of flavanols, by weight of the red grape extract.

As used herein, "red grape extract" preferably refers to red grape skin extracts, and may optionally include extracts from other fruits and vegetables, including black currant (*Ribes nigrum*) and carrots (*Daucus carota*). The red grape extract may be obtained from a variety of red grape sources, including those of the genus Vitis. For example, the red grape extract may be obtained from *Vitis vinifera L.* (typically cultivated in Europe), *Vitis labrusco*, and *Vitis rotundifolia* (both typically cultivated in North America), preferably from *Vitis vinifera L.*

Red grape extract may be provided according to known methods in the art, for example, through crushing, pressing, extraction, filtering (several times), and concentration of the extract by vacuum evaporation, and well as freezing. It is highly preferable that only water is utilized for this extraction process, with some addition of invert sugar and citric acid. Preferably, no additional components, for example, solvents (including organic solvents and sulfur dioxide), carriers, or preservatives, are added to the extract itself. The process preferably maintains the flavanols, including anthocyanins, as well as carotenoids. Additionally, the process preferably eliminates other constituents present in the red grape, for example, a majority of sugars, acids, and minerals.

A non-limiting, but preferred, example of a commercially available red grape extract is Nutrifood®, commercially available from GNT International, Netherlands.

Wherein red grape extract is included herein, this will also typically correlate to including from about 0.001% to about 20% of red grape extract, more preferably from about 0.01% to about 10% red grape extract, even more preferably from about 0.1% to about 5% red grape extract, and most preferably from about 1% to about 3% red grape extract.

Glycerol

The present inventors have even further discovered that the mammalian skin hydrating effect provided by the flavanols is surprisingly enhanced wherein glycerol is included within the composition. The glycerol is an optional, but highly preferred, component herein.

It has been reported that glycerol may be administered orally for cellular hydration of athletes. See e.g., Wagner, "Hyperhydrating with Glycerol: Implications for Athletic Performance", Journal of the American Dietetic Association, Volume 99(2), pp. 207–212 (Feb. 1999). However, surprisingly, the present inventors have discovered that in addition to this cellular effect, glycerol may be administered orally to provide a mammalian skin hydration effect.

Accordingly, the most preferred embodiments of the present invention include glycerol (also commonly referred to as glycerin). Preferably, the glycerol is food-grade.

As is commonly known, glycerol is a naturally occurring 3-carbon polyalcohol having the chemical name 1,2,3-propanetriol. Precursors of glycerol which are capable of metabolism by the human body are also included within the term "glycerol", for example, biohydrolyzable esters of glycerol, preferably those which are substituted at the 1 and/or 3 position of the glycerol backbone.

Glycerol is commercially available from a variety of sources including, for example, Aldrich Chemical Co., Milwaukee, Wis. Additionally, a highly preferred source is marketed under the name Superol®, commercially available from Procter & Gamble Co. Alternatively, glycerol may be produced by synthetic means, for example through synthetic hydration of epichlorohydrin followed by reaction with sodium hydroxide, reaction of allyl alcohol with hydrogen peroxide, or reaction of allyl alcohol with peracetic acid followed by hydrolysis. Glycerol is also a by-product in soap and fatty acid manufacturing.

The present inventors have discovered that the mammalian skin hydrating effect provided by the flavanols herein is synergistically enhanced wherein from about 0.0001% to about 20% of glycerol, more preferably from about 0.001% to about 20% of glycerol, still more preferably from about 0.01% to about 15% of glycerol, even more preferably from about 0.1% to about 10% of glycerol, and most preferably from about 2% to about 5% of glycerol is included within a composition, all by weight of the composition.

Aloe

The present inventors have discovered that the mammalian skin hydrating effect provided by the flavanols herein is also surprisingly enhanced wherein the juice or gel of a plant of the genus Aloe is included within the composition. While the benefits of topical application of aloe to treat for example, skin burns, inflammatory conditions (e.g., eczema), skin abrasions and bruises, and herpes complex is commonly known, the inventors herein have surprisingly discovered that inclusion of aloe in the compositions herein provides a mammalian skin hydrating effect.

Accordingly, preferred embodiments of the present invention include, in addition to one or more flavanols, the juice or gel derived from a plant of the genus Aloe (the juice or gel of this genus is herein referred to for simplicity as "aloe"). The aloe is an optional component herein.

The genus Aloe comprises about 600 species of plant. See e.g., Capasso et al., "Aloe and Its Therapeutic Use", *Phytotherapy Research*, Vol. 12, S124–S127 (1998). Non-limiting examples of species of the genus Aloe, from which the aloe herein may be derived, include Aloe ferox Miller, *Aloe africana* Miller, *Aloe spicata* Baker, *Aloe chinensis* Bak, *Aloe barbadensis* Miller, and *Aloe arborescens* Miller. More preferably, the aloe herein is derived from *Aloe barbadensis* Miller (commonly found in, for example, Central America and commonly known as Aloe vera) and *Aloe arborescens* Miller. Most preferably, the aloe herein is derived from *Aloe barbadensis* Miller.

The aloe herein (the aloe juice or gel) is primarily composed of the mucilaginous parenchymous tissue which is commonly excised from fresh leaves of the plant and immediately utilized as the obtained juice or gel, or dried (e.g., lyophilized) until use. However, it is preferable to use the fresh aloe (not dried) in the composition herein. The aloe contains primarily glycoproteins, saccharides, and enzymes. The polysaccharides are primarily partially acetylated glucomannans which differ in their glucose to mannose ratio, in degree of acetylation, the linearity or branching of the polysaccharide, and molecular weight. Other saccharides within the aloe include cellulose, glucose, mannose, L-rhammnose, and aldopentose. Enzymes within the aloe include oxidase, amylase, catalase, lipase, and alkaline phsophatase. Other components within the aloe include cholesterol, triglycerides, steroids, β-sitosterol, lignins, uric acid, gibberellin, lectin-like substances, and salicylic acid. See e.g., Shelton, "Aloe Vera: Its Chemical and Therapeutic Properties", *International Journal of Dermatology*, Vol. 30(10), pp. 679–683 (October 1991).

The aloe herein may be obtained by any of a variety of methods commonly known in the art, or may be commercially available from a variety of sources which manufacture bulk supplies of the aloe juice or gel. For example, as stated above, the mucilaginous parenchymous tissue may be excised from leaves of the plant. The aloe herein may be obtained from extraction of the leaves from an aqueous ethanolic mixture or water mixtures (including hot water extracts). See e.g., Joshi, "Chemical Constituents and Biological Activity of *Aloe barbadensis*", *Journal of Medicinal and Aromatic Plant Sciences*, Vol. 20, pp. 768–773 (1998); Cappaso et al., p. S124; and Shelton, "Aloe Vera: Its Chemical and Therapeutic Properties", *International Journal of Dermatology*, Vol. 30(10), pp. 679–683 (Oct. 1991). Grindlay, "The Aloe Vera Phenomenon: A Review of the Properties and Modern Uses of the Leaf Parenchyma Gel", *Journal of Ethnophannacology*, Vol. 16, pp. 117–151 (1986) sets forth a non-limiting example of preparation of the aloe herein. Briefly, the leaves of the whole Aloe plant are cleaned, soaked, and sprayed with water and a mild chlorine solution. Alternatively, the leaves are washed by hand, using brushes for scrubbing. The outer layers of the leaf, including the aloe latex (pericyclic cells) are removed by filleting with a knife to remove the central "fillet" of gel. Care is taken not to tear the green rind which can cause contamination with the aloe latex.

The aloe herein is substantially free of anthraquinones, such to avoid the laxative affect associated with these components (which can contribute to a dehydrating effect). The anthraquinones typically contained within a whole Aloe plant include barbaloin (also known as aloin (10-(1',5'-anhydroglucosyl)-aloe-emodin-9-anthrone), isobarbaloin, anthranol, aloetic acid, anthracene, ester of cinnamic acid, aloe-emodin, emodin, chrysophanic acid, ethereal oil, and resistannol (components naturally occurring in what is commonly known as the aloe latex). See e.g., Shelton, "Aloe Vera: Its Chemical and Therapeutic Properties", *International Journal of Dermatology*, Vol. 30(10), pp. 679–683 (October 1991). These anthraquinones occur within the yellow matter containing specialized pericyclic cells of the plant. With respect to anthraquinones, the term "substantially free" means that less than about 25% of the aloe is barbaloin and isobarbaloin, by weight of the "aloe", preferably less than about 15%, more preferably less than about 10%, even more preferably less than about 5%, and most preferably less than about 2%. Methods of separating anthraquinones (and the aloe latex) from the "aloe" (again, herein the aloe juice or gel) are commonly known in the art. See e.g., Cappaso et al., p. S124.

The present inventors have discovered that the mammalian skin hydrating effect provided by the flavanols herein is synergistically enhanced wherein from about 0.0001% to about 15% of aloe, more preferably from about 0.001% to about 10% of aloe, still more preferably from about 0.01% to about 10% of aloe, even more preferably from about 0.1% to about 5% of aloe, and most preferably from about 0.5% to about 2% of aloe is included within a composition, all by weight of the composition.

Kits of the Present Invention

The present invention further relates to kits comprising a composition as described herein and information that use of the composition provides hydration of mammalian skin. Preferably, the composition is a beverage composition. As stated, the present compositions must comprise one or more flavanols which, as the present inventors have discovered, provides skin health benefits including hydration of mammalian skin. Particularly preferred compositions which may be included within the kit are described herein throughout.

Such information, for example, may be oral information disseminated as part of the kit, but is preferably written information, typically present on packaging associated with the composition (e.g., a label present on a package containing the composition or package insert included within the kit). As used herein, "written" means information disseminated through words, pictures, symbols, and/or other visible information. Such information need not utilize the actual words "hydration", "human", "mammal", or "skin", but rather use of words, pictures, symbols, and the like conveying the same or similar meaning are contemplated within the scope of this invention. Such information may also include information about general skin health and reasons for which skin health, and particularly skin hydration, is important for the user (for example, for treating dry or undernourished skin, and fine lines and wrinkles).

Methods of the Present Invention

In accordance with the present invention, methods of hydrating mammalian skin are provided through orally administering to a mammal, preferably a human, a composition as has been described herein. As stated, the present compositions must comprise one or more flavanols which, as the present inventors have discovered, provides skin health benefits including hydration of mammalian skin. Particularly preferred compositions which may be orally administered according to this method are described herein throughout.

As used herein, the term "orally administering" with respect to the mammal (preferably, human) means that the mammal ingests or is directed to ingest (preferably, for the purpose of hydrating mammalian skin) one or more compositions of the present invention. Preferably, the composition is a beverage composition. Wherein the mammal is directed to ingest one or more of the compositions, such direction may be that which instructs and/or informs the user that use of the composition may and/or will hydrate mammalian, preferably human, skin for various purposes including, for example, treating dry or undernourished skin, and fine lines and wrinkles. For example, such direction may be oral direction (e.g., through oral instruction from, for example, a physician, dermatological professional, sales professional or organization, and/or radio or television media (i.e., advertisement) or written direction (e.g., through written direction from, for example, a physician or dermatological professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" means through words, pictures, symbols, and/or other visible descriptors. Such direction need not utilize the actual words "hydration", "human", "mammal", or "skin", but rather use of words, pictures, symbols, and the like conveying the same or similar meaning are contemplated within the scope of this invention.

Use of the Present Compositions and Kits

The compositions described herein are useful in a wide variety of finished products, including pharmaceutical, food, and beverage compositions. Preferably, the products are useful for providing a mammalian skin hydrating benefit, and are used in beverage compositions, as has been described herein.

Such beverage compositions may be dilute water beverages (also called "near-water" beverages), milks, coffees, teas, colas, and fruit juices, preferably teas and fruit juices, and often preferably a tea and fruit juice combination.

Various optional elements may be incorporated into the compositions of the present invention. Non-limiting examples of optional elements are as follows:

Water

Water may be included in the compositions of the present invention, particularly wherein the compositions are beverage compositions. As used herein, the term "water" includes the total amount of water present in the composition. "Water" includes water from flavor agents, sugar syrups, and other sources, e.g., gum solutions. Water of hydration of, for example, calcium and other solids, is also included. Wherein water is included, water is preferably included at levels from about 0.1% to about 99.999%, more preferably from about 5% to about 99%, still more preferably at least about 50%, even more preferably at least about 70%, and most preferably from about 70% to about 95%, by weight of the composition.

Beverage Emulsions

Dilute juice beverages of the present invention may optionally, but preferably, comprise from about 0.2% to about 5%, preferably from about 0.5% to about 3%, and most preferably from about 0.8% to about 2%, of a beverage emulsion. This beverage emulsion can be either a cloud emulsion or a flavor emulsion.

For cloud emulsions, the clouding agent can comprise one or more fats or oils stabilized as an oil-in-water emulsion using a suitable food grade emulsifier. Any of a variety of fats or oils may be employed as the clouding agent, provided that the fat or oil is suitable for use in foods and/or beverages. Preferred are those fats and oils that have been refined, bleached and deodorized to remove off-flavors. Especially suitable for use as clouding agents are those fats that are organoleptically neutral. These include fats from the following sources: vegetable fats such as soybean, corn, safflower, sunflower, cottonseed, canola, and rapeseed; nut fats such as coconut, palm, and palm kernel; and synthetic fats. See e.g., Kupper et al., U.S. Pat. No. 4,705,691, issued Nov. 10, 1987, for suitable fat or oil clouding agents.

Any suitable food grade emulsifier can be used that can stabilize the fat or oil clouding agent as an oil-in-water emulsion. Suitable emulsifiers include gum acacia, modified food starches (e.g., alkenylsuccinate modified food starches), anionic polymers derived from cellulose (e.g., carboxymethylcellulose), gum ghatti, modified gum ghatti, xanthan gum, tragacanth gum, guar gum, locust bean gum, pectin, and mixtures thereof. See e.g., Kupper et al., U.S. Pat. No. 4,705,691, issued Nov. 10, 1987. Modified starches treated to contain hydrophobic as well as hydrophilic groups, such as those described in Caldwell et al., U.S. Pat. No. 2,661,349, are preferred emulsifiers for use as herein. Octenyl succinate (OCS) modified starches such as those described in Marotta et al., U.S. Pat. No. 3,455,838 and Barndt et al., U.S. Pat. No. 4,460,617 are especially preferred emulsifiers.

The clouding agent can be combined with a weighting agent to provide a beverage opacifier that imparts a total or partial opaque effect to the beverage without separating out and rising to the top. The beverage opacifier provides the appearance to the consumer of a juice-containing beverage. Any suitable weighting oil can be employed in the beverage opacifier. Typical weighting oils include brominated vegetable oil, glycerol ester of wood rosin (ester gum), sucrose acetate isobutyrate (SAIB) and other sucrose esters, gum damar, colophony, gum elemi, or others known to those skilled in the art. Other suitable weighting agents include brominated liquid polyol polyesters which are nondigestible. See e.g., Brand et al., U.S. Pat. No. 4,705,690, issued Nov. 10, 1987.

The cloud/opacifier emulsion is prepared by mixing the clouding agent with the weighting agent (for opacifier emulsions), the emulsifier and water. The emulsion typically contains from about 0.1% to about 25% clouding agent, from about 1% to about 20% weighting oil agent (in the case of opacifier emulsions), from about 1% to about 30% emulsifiers, and from about 25% to about 97.9% water (or quantum satis).

The particle size of the water-insoluble components of the emulsion is reduced by employing a suitable apparatus known in the art. Because the ability of emulsifying agents to hold oil in suspension is proportional to particle size, emulsions of particles with diameters of about 0.1 to about 3.0 microns are suitable. Preferably, the particles are about 2.0 microns or less in diameter. Most preferred is an emulsion in which substantially all the particles are 1.0 microns or less in diameter. The particle size is reduced by passing the mixture through an homogenizer, colloid mill or turbine-type agitator. Usually one or two passes is sufficient. See e.g., Kupper et al., U.S. Pat. No. 4,705,691, issued Nov. 10, 1987.

Flavor emulsions useful in beverage products of the present invention comprise one or more suitable flavor oils, extracts, oleoresins, essential oils and the like, known in the art for use as flavorants in beverages. This component can also comprise flavor concentrates such as those derived from concentration of natural products such as fruits. Terpeneless citrus oils and essences can also be used herein. Examples of suitable flavors include, for example, fruit flavors such as orange, lemon, lime and the like, cola flavors, tea flavors, coffee flavors, chocolate flavors, dairy flavors. These flavors can be derived from natural sources such as essential oils and extracts, or can be synthetically prepared. The flavor emulsion typically comprises a blend of various flavors and can be employed in the form of an emulsion, alcoholic extract, or spray dried. The flavor emulsion can also include clouding agents, with or without weighting agents, as previously described. See e.g., Kupper et al., U.S. Pat. No. 4,705,691, issued Nov. 10, 1987.

Flavor emulsions are typically prepared in the same manner as cloud/opacifier emulsions by mixing one or more flavoring oils (from about 0.001% to about 20%) with an emulsifying agent (from about 1% to about 30%) and water. (The oil clouding agents can also be present). Emulsions of particles with diameters of from about 0.1 to about 3.0 microns are suitable. Preferably, the particles are about 2.0 microns or less in diameter. Most preferably, the particles are about 1.0 microns or less in diameter. The emulsifying agent coats the particularized flavor oil to aid in preventing coalescence and in maintaining an appropriate dispersion. The viscosity and specific gravity of the flavor emulsion are regulated to be compatible with the finished beverage. See e.g., Kupper et al., U.S. Pat. No. 4,705,691, issued Nov. 10, 1987.

Flavor Agents

The compositions herein may optionally, but preferably, comprise one or more flavor agents. Preferably, such flavor agents are included in the beverage compositions and are typically selected from fruit juice, milk solids, fruit flavors, botanical flavors, and mixtures thereof. Wherein fruit juice is included, the beverages of the present invention can comprise from about 0.1% to about 99%, preferably from about 1% to about 50%, more preferably from about 2% to about 15%, and most preferably from about 3% to about 6%, fruit juice. (As measured herein, the weight percentage of fruit juice is based on a single strength 2° to 16° Brix fruit juice). The fruit juice can be incorporated into the beverage as a puree, comminute, or as a single strength or concentrated juice. Especially preferred is incorporation of the fruit juice as a concentrate with a solids content (primarily as sugar solids) of from about 20° to about 80° Brix.

The fruit juice can be any citrus juice, non-citrus juice, or mixture thereof, which are known for use in dilute juice beverages. The juice can be derived from, for example, apple, cranberry, pear, peach, plum, apricot, nectarine, grape, cherry, currant, raspberry, gooseberry, elderberry, blackberry, blueberry, strawberry, lemon, lime, mandarin, orange, grapefruit, cupuacu, potato, tomato, lettuce, celery, spinach, cabbage, watercress, dandelion, rhubarb, carrot, beet, cucumber, pineapple, coconut, pomegranate, kiwi, mango, papaya, banana, watermelon, passion fruit, tangerine, and cantaloupe. Preferred juices are derived from apple, pear, lemon, lime, mandarin, grapefruit, cranberry, orange, strawberry, tangerine, grape, kiwi, pineapple, passion fruit, mango, guava, raspberry and cherry. Citrus juices, preferably grapefruit, orange, lemon, lime, and mandarin juices, as well as juices derived from mango, apple, passion fruit, and guava, as well as mixtures of these juices are most preferred.

Fruit flavors may also be utilized. As described above with respect to flavor emulsions, fruit flavors may be derived from natural sources such as essential oil and extracts, or can be synthetically prepared. Fruit flavors may be derived from fruits through processing, particularly concentrating. Wherein fruit juices are concentrated or evaporated, the water which is removed or the condensate contains volatile substances which comprise the flavor of the fruit. Often, such flavor is added to a juice concentrate to enhance the flavor thereof. The condensate may also be used to flavor "near waters" (lightly flavored water).

Botanical flavors may also be utilized. As used herein, the term "botanical flavor" refers to a flavor derived from parts of a plant other than the fruit; i.e., derived from nuts, bark, roots, and/or leaves. Also included within the term "botanical flavor" are synthetically prepared flavors made to simulate botanical flavors derived from natural sources. Botanical flavors can be derived from natural sources such as essential oils and extracts, or can be synthetically prepared. Suitable botanical flavors include jamaica, kola, marigold, chrysanthemum, chamomile, ginger, valerian, yohimbe, hops, eriodictyon, ginseng, bilberry, rice, red wine, mango, peony, lemon balm, nut gall, oak chip, lavender, walnut, gentiam, luo han guo, cinnamon, angelica, aloe, agrimony, yarrow and mixtures thereof.

Beverages according to the present invention may also comprise milk solids. These milk solids can be derived from various sources including whole milk, skim milk, condensed milk, and dried milk powder. As used herein, the term "milk" will be used to describe an aqueous dispersion of milk solids, such as fluid (whole or skim milk) or non-fat dry milk or condensed milk diluted with water. The amount of milk included typically ranges from about 0.001% to about 99.8%, preferably from about 0.01% to about 50%, more preferably from about 0. 1% to about 10%, and most preferably from about 0.5% to about 5%, by weight of the composition.

Thickeners and Bulking Agents

Food and beverage compositions according to the present invention can further comprise thickeners, including xanthan gum, carboxymethylcellulose, carboxyethylcellulose, hydroxypropylcellulose, methylcellulose, microcrystalline cellulose, starches, dextrins, fermented whey, tofu, maltodextrins, polyols, including sugar alcohols (e.g., sorbitol and mannitol), carbohydrates (e.g., lactose), propylene glycol alginate, gellan gum, guar gum, pectin, tragacanth gum, gum acacia, locust bean gum, gum arabic, gelatin, as well as mixtures of these thickeners. These thickeners are typically included in the compositions of the present invention at levels up to about 0.1%, depending on the particular thickener involved and the viscosity effects desired.

Sweeteners

The food and beverage compositions of the present invention can, and typically will, contain an effective amount of one or more sweeteners, including carbohydrate sweeteners and natural and/or artificial no/low calorie sweeteners. The amount of the sweetener used in the compositions of the present invention typically depends upon the particular sweetener used and the sweetness intensity desired. For no/low calorie sweeteners, this amount varies depending upon the sweetness intensity of the particular sweetener.

The compositions of the present invention can be sweetened with any of the carbohydrate sweeteners, preferably monosaccharides and/or disaccharides. Sweetened compositions, particularly beverages, will typically comprise from about 0.1% to about 40%, more preferably from about 0.1% to about 20%, and most preferably from about 6 to about 14%, sweetener. These sweeteners can be incorporated into the compositions in solid or liquid form but are typically, and preferably, incorporated as a syrup, most preferably as a concentrated syrup such as high fructose corn syrup. For purposes of preparing beverages of the present invention, these sugar sweeteners can be provided to some extent by other components of the beverage such as, for example, the fruit juice component and/or flavors.

Preferred sugar sweeteners for use in compositions of the present invention are sucrose, fructose, glucose, and mixtures thereof. Fructose can be obtained or provided as liquid fructose, high fructose corn syrup, dry fructose or fructose syrup, but is preferably provided as high fructose corn syrup. High fructose corn syrup (HFCS) is commercially available as HFCS-42, HFCS-55 and HFCS-90, which comprise 42%, 55% and 90%, respectively, by weight of the sugar solids therein, as fructose. Other naturally occurring sweeteners or their purified extracts, such as glycyrrhizin, the protein sweetener thaumatin, the juice of Luo Han Guo disclosed in, for example, Fischer et al., U.S. Pat. No. 5,433,965, issued Jul. 18, 1995, and the like can also be used in the compositions of the present invention.

Suitable no/low calorie sweeteners include saccharin, cyclamates, L-aspartyl-L-phenylalanine lower alkyl ester sweeteners (e.g., aspartame); L-aspartyl-D-alanine amides disclosed in Brennan et al., U.S. Pat. No. 4,411,925; L-aspartyl-D-serine amides disclosed in Brennan et al., U.S.

Pat. No. 4,399,163; L-aspartyl-L-1-hydroxymethylalkaneamide sweeteners disclosed in Brand, U.S. Pat. No. 4,338,346; L-aspartyl-1-hydroxyethyalkaneamide sweeteners disclosed in Rizzi, U.S. Pat. No. 4,423,029; L-aspartyl-D-phenylglycine ester and amnide sweeteners disclosed in Janusz, European Patent Application 168,112, published Jan. 15, 1986; N-[N-3,3-dimethylbutyl)-L-α-aspartyl]-L-phenylalanine 1-methyl ester sweeteners disclosed in Gerlat et al., WO 99/30576, assigned to The Nutrasweet Co., published Jun. 24, 1999; alltame, thaumatin; dihydrochalcones; cyclamates; steviosides; glycyrrhizins, synthetic alkoxy aromatics, such as Dulcin and P-4000; sucralose; suosan; miraculin; monellin; sorbitol, xylitol; talin; cyclohexylsulfamates; substituted imidazolines; synthetic sulfamic acids such as acesulfame, acesulfame-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates; and the like and mixtures thereof. A particularly preferred low calorie sweetener is aspartame.

Coloring Agent

Small amounts of coloring agents may be utilized in the compositions of the present invention. FD&C dyes (e.g., yellow #5, blue #2, red #40) and/or FD&C lakes are preferably used. By adding the lakes to the other powdered ingredients, all the particles, in particular the colored iron compound, are completely and uniformly colored and a uniformly colored composition is attained. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and β-carotene may also be used. The exact amount of coloring agent used will vary, depending on the agents used and the intensity desired in the finished product. The amount can be readily determined by one skilled in the art. Generally, if utilized, the coloring agent should be present at a level of from about 0.0001% to about 0.5%, preferably from about 0.001% to about 0.1%, and most preferably from about 0.004% to about 0.1%, by weight of the composition.

Nutrients

The compositions herein (particularly the food and beverage compositions) can be fortified with one or more nutrients, especially one or more vitamins and/or minerals. The U.S. Recommended Daily Intake (USRDI) for vitamins and minerals are defined and set forth in the Recommended Daily Dietary Allowance-Food and Nutrition Board, National Academy of Sciences-National Research Council.

Unless otherwise specified herein, wherein a given mineral is present in the product, the product comprises at least about 1%, preferably at least about 5%, more preferably from about 10% to about 200%, even more preferably from about 40% to about 150%, and most preferably from about 60% to about 125% of the USRDI of such mineral. Unless otherwise specified herein, wherein a given vitamin is present in the product, the product comprises at least about 1%, preferably at least about 5%, more preferably from about 10% to about 200%, even more preferably from about 20% to about 150%, and most preferably from about 25% to about 120% of the USRDI of such vitamin.

Non-limiting examples of such vitamins and minerals include iron, zinc, copper, calcium, phosphorous, niacin, thiamin, folic acid, pantothenic acid, iodine, vitamin A, vitamin C, vitamin $B_2$, vitamin $B_3$, vitamin $B_6$, vitamin $B_{12}$, vitamin D, vitamin E, and vitamin K. Preferably, wherein a vitamin or mineral is utilized the vitamin or mineral is selected from iron, zinc, calcium, niacin, thiamin, folic acid, iodine, vitamin A, vitamin C, vitamin $B_6$, vitamin $B_{12}$, vitamin D, and vitamin E. A particularly preferred mineral for use herein is calcium.

Commercially available vitamin A sources may also be included in the present compositions. As used herein, "vitamin A" includes, but is not limited to, retinol, β-carotene, retinol palmitate, and retinol acetate. The vitamin A may be in the form of, for example, an oil, beadlets or encapsulated.

Wherein vitamin A is present in the compositions herein, the product comprises at least about 1%, preferably at least about 5%, more preferably from about 10% to about 200%, even more preferably from about 15% to about 150%, and most preferably from about 20% to about 120% of the USRDI of such vitamin. Wherein vitamin A is present in the products herein, it is especially preferred to include about 25% of the USRDI of vitamin A. The quantity of vitamin A to be added is dependent on processing conditions and the amount of vitamin A deliver desired after storage. Preferably, wherein vitamin A is included within the present compositions, the products comprise from about 0.0001% to about 0.2%, more preferably from about 0.0002% to about 0.12%, also preferably from about 0.0003% to about 0.1%, even more preferably from about 0.0005% to about 0.08%, and most preferably from about 0.001% to about 0.06% of vitamin A, by weight of the composition.

Commercially available sources of vitamin $B_2$ (also known as riboflavin) may be utilized in the present compositions. Wherein vitamin $B_2$ is present in the compositions herein, the product comprises at least about 1%, preferably at least about 5%, more preferably from about 5% to about 200%, even more preferably from about 10% to about 150%, and most preferably from about 10% to about 120% of the USRDI of such vitamin. Wherein vitamin $B_2$ is present in the compositions herein, it is especially preferred to include from about 15% to about 35% of the USRDI of vitamin $B_2$.

Commercially available sources of vitamin C can be used herein. Encapsulated ascorbic acid and edible salts of ascorbic acid can also be used. Wherein vitamin C is present in the products herein, the product comprises at least about 1%, preferably at least about 5%, more preferably from about 10% to about 200%, even more preferably from about 20% to about 150%, and most preferably from about 25% to about 120% of the USRDI of such vitamin. Wherein vitamin C is present in the compositions herein, it is especially preferred to include about 100% of the USRDI of vitamin C. The quantity of vitamin C to be added is dependent on processing conditions and the amount of vitamin C deliver desired after storage. Preferably, wherein vitamin C is included within the present compositions, the compositions comprise from about 0.005% to about 0.2%, more preferably from about 0.01% to about 0.12%, also preferably from about 0.02% to about 0.1%, even more preferably from about 0.02% to about 0.08%, and most preferably from about 0.03% to about 0.06% of vitamin C, by weight of the composition.

Commercial sources of iodine, preferably as an encapsulated iodine may be utilized herein. Other sources of iodine include iodine-containing salts, e.g., sodium iodide, potassium iodide, potassium iodate, sodium iodate, or mixtures thereof. These salts may be encapsulated.

Nutritionally supplemental amounts of other vitamins which may be incorporated herein include, but are not limited to, vitamins $B_6$ and $B_{12}$, folic acid, niacin, pantothenic acid, folic acid, vitamin D, and vitamin E. Wherein the composition comprises one of these vitamins, the product preferably comprises at least 5%, preferably at least 25%, and most preferably at least 35% of the USRDI for such vitamin.

Minerals which may optionally be included in the composition herein are, for example, magnesium, zinc, iodine, iron, calcium, and copper. Any soluble salt of these minerals suitable for inclusion edible products can be used, for example, magnesium citrate, magnesium gluconate, magnesium sulfate, zinc chloride, zinc sulfate, potassium iodide, copper sulfate, copper gluconate, and copper citrate.

Calcium is a particularly preferred mineral for use in the present invention. Preferred sources of calcium include, for example, amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium titrate, calcium gluconate, calcium realate, calcium tantrate, and calcium lactate, and in particular calcium citrate-malate. The form of calcium citrate-malate is described in, e.g., Mehansho et al., U.S. Pat. No. 5,670,344, issued Sep. 23, 1997; Diehl et al., U.S. Pat. No. 5,612,026, issued Mar. 18, 1997; Andon et al., U.S. Pat. No. 5,571,441, issued Nov. 5, 1996; Meyer et al., U.S. Pat. No. 5,474,793, issued Dec. 12, 1995; Andon et al., U.S. Pat. No. 5,468,506, issued Nov. 21, 1995; Burkes et al., U.S. Pat. No. 5,445,837, issued Aug. 29, 1995; Dake et al., U.S. Pat. No. 5,424,082, issued Jun. 13, 1995; Burkes et al., U.S. Pat. No. 5,422,128, issued Jun. 6, 1995; Burkes et al., U.S. Pat. No. 5,401,524, issued Mar. 28, 1995; Zuniga et al., U.S. Patent No. 5,389, 387, issued Feb. 14, 1995; Jacobs, U.S. Pat. No. 5,314,919, issued May 24, 1994; Saltman et al., U.S. Pat. No. 5,232, 709, issued Aug. 3, 1993; Camden et al., U.S. Pat. No. 5,225,221, issued Jul. 6, 1993; Fox et al., U.S. Pat. No. 5,215,769, issued Jun. 1, 1993; Fox et al., U.S. Pat. No. 5,186,965, issued Feb. 16, 1993; Saltman et al., U.S. Pat. No. 5,151,274, issued Sep. 29, 1992; Kochanowski, U.S. Pat. No. 5,128,374, issued Jul. 7, 1992; Mehansho et al., U.S. Pat. No. 5,118,513, issued Jun. 2, 1992; Andon et al., U.S. Pat. No. 5,108,761, issued Apr. 28, 1992; Mehansho et al., U.S. Pat. No. 4,994,283, issued Feb. 19, 1991; Nakel et al., U.S. Pat. No. 4,786,510, issued Nov. 22, 1988; and Nakel et al., U.S. Pat. No. 4,737,375, issued Apr. 12, 1988. Preferred compositions of the present invention will comprise from about 0.01% to about 0.5%, more preferably from about 0.03% to about 0.2%, even more preferably from about 0.05% to about 0.15%, and most preferably from about 0.1% to about 0.15% of calcium, by weight of the composition.

Iron may also be utilized in the compositions of the present invention. Acceptable forms of iron are well-known in the art. The amount of iron compound incorporated into the composition will vary widely depending upon the level of supplementation desired in the final product and the targeted consumer. Iron fortified compositions of the present invention typically contain from about 5% to about 100%, preferably from about 15% to about 50%, and most preferably about 20% to about 40% of the USRDI for iron.

Ferrous iron is typically better utilized by the body than ferric iron. Highly bioavailable ferrous salts that can be used in the ingestible compositions of the present invention are ferrous sulfate, ferrous fumarate, ferrous succinate, ferrous gluconate, ferrous lactate, ferrous tartarate, ferrous citrate, ferrous amino acid chelates, as well as mixtures of these ferrous salts. While ferrous iron is typically more bioavailable, certain ferric salts can also provide highly bioavailable sources of iron. Highly bioavailable ferric salts that can be used in the food or beverage compositions of the present invention are ferric saccharate, ferric ammonium citrate, ferric citrate, ferric sulfate, as well as mixtures of these ferric salts. Combinations or mixtures of highly bioavailable ferrous and ferric salts can be used in these edible mixes and ready-to-serve beverages. The preferred sources of highly bioavailable iron are ferrous fumarate and ferrous amino acid chelates.

Ferrous amino acid chelates particularly suitable as highly bioavailable iron sources for use in the present invention are those having a ligand to metal ratio of at least 2:1. For example, suitable ferrous amino acid chelates having a ligand to metal mole ratio of two are those of formula:

where L is an alpha amino acid, dipeptide, tripeptide, or quadrapeptide ligand. Thus, L can be any ligand which is a naturally occurring alpha amino acid selected from alanine, arginine, asparagine, aspartic acid, cysteine, cystine, glutamine, glutamic acid, glycine, histidine, hydroxyproline, isoleucine, leucine, lysine, methionine, omithine, phenylalanine, proline, serine, threonine, tryptophan, tyrosine, and valine; or dipeptides, tripeptides, or quadrapeptides formed by any combination of these alpha amino acids. See e.g., Ashmead et al., U.S. Pat. No. 4,863,898, issued Sep. 5, 1989; Ashmead, U.S. Pat. No. 4,830,716, issued May 16, 1989; and Ashmead, U.S. Patent No. 4,599, 152, issued Jul. 8, 1986, all of which are incorporated by reference. Particularly preferred ferrous amino acid chelates are those where the reacting ligands are glycine, lysine, and leucine. Most preferred is the ferrous amino acid chelate sold under the mark Ferrochel® (Albion Laboratories, Salt Lake City, Utah) wherein the ligand is glycine.

In addition to these highly bioavailable ferrous and ferric salts, other sources of bioavailable iron can be included in the food and beverage compositions of the present invention. Other sources of iron particularly suitable for fortifying products of the present invention included certain iron-sugar-carboxylate complexes. In these iron-sugar-carboxylate complexes, the carboxylate provides the counterion for the ferrous (preferred) or ferric iron. The overall synthesis of these iron-sugar-carboxylate complexes involves the formation of a calcium-sugar moiety in aqueous media (for example, by reacting calcium hydroxide with a sugar, reacting the iron source (such as ferrous ammonium sulfate) with the calcium-sugar moiety in aqueous media to provide an iron-sugar moiety, and neutralizing the reaction system with a carboxylic acid (the "carboxylate counterion") to provide the desired iron-sugar-carboxylate complex. Sugars that can be used to prepare the calcium-sugar moiety include any of the ingestible saccharidic materials, and mixtures thereof, such as glucose, sucrose and fructose, mannose, galactose, lactose, maltose, and the like, with sucrose and fructose being the more preferred. The carboxylic acid providing the "carboxylate counterion" can be any ingestible carboxylic acid such as citric acid, malic acid tartaric acid, lactic acid, succinic acid, propionic acid, etc., as well as mixtures of these acids.

These iron-sugar-carboxylate complexes can be prepared in the manner described in, e.g., Nakel et al., U.S. Pat. Nos. 4,786,510 and 4,786,518, issued Nov. 22, 1988, both of which are incorporated by reference. These materials are referred to as "complexes", but they may exist in solution as complicated, highly hydrated, protected colloids; the term "complex" is used for the purpose of simplicity.

Zinc may also be utilized in the compositions of the present invention. Acceptable forms of zinc are well-known in the art. Zinc fortified products of the present invention typically contain from about 5% to about 100%, preferably from about 15% to about 50%, and most preferably about 25% to about 45% of the USRDI for zinc. The zinc compounds which can be used in the present invention can be in any of the commonly used forms such as, e.g., zinc sulfate, zinc chloride, zinc acetate, zinc gluconate, zinc ascorbate, zinc citrate, zinc aspartate, zinc picolinate, amino acid chelated zinc, and zinc oxide. Zinc gluconate and amino acid chelated zinc are particularly preferred.

Fiber Component

Food and beverage compositions can be made which further comprise one or more dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

Particularly preferred fibers for use herein are glucose polymers, preferably those which have branched chains, and which are typically less digestable relative to starches and maltodextrins. Preferred among these fibers is one marketed under the trade name Fiβersol2, commercially available from Matsutani Chemical Industry Co., Itami City, Hyogo, Japan.

Pectin and fructo-oligosaccharides are also preferred fibers herein. Even more preferably, pectin and fructo-oligosaccharides are used in combination. The preferred ratio of pectin to fructo-oligosaccharide is from about 3:1 to about 1:3, by weight of the composition. The preferred pectins have a degree of esterification higher than about 65%.

The preferred fructo-oligosaccharides are a mixture of fructo-oligosaccharides composed of a chain of fructose molecules linked to a molecule of sucrose. Most preferably, they have a nystose to kestose to fructosyl-nystose ratio of about 40:50:10, by weight of the composition. Preferred fructo-oligosaccharides may be obtained by enzymatic action of fructosyltransferase on sucrose such as those which are, for example, commercially available from Beghin-Meiji Industries, Neuilly-sur-Seine, France. Preferred pectins are obtained by hot acidic extraction from citrus peels and may be obtained, for example, from Danisco Co., Braband, Denmark.

These dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Wherein a soluble fiber is utilized, the desired total level of soluble dietary fiber for the present compositions of the present invention is from about 0.01% to about 15%, preferably from about 0.1% to about 5%, more preferably from about 0.1% to about 3%, and most preferably from about 0.2% to about 2%. The total amount of soluble dietary fiber includes any added soluble dietary fiber as well as any soluble dietary fiber naturally present in any other component of the present invention.

Carbonation Component

Carbon dioxide can be introduced into the water which is mixed with a beverage syrup or into the dilute beverage after dilution to achieve carbonation. The carbonated beverage can be placed into a container, such as a bottle or can, and then sealed. Any conventional carbonation methodology may be utilized to make carbonated beverage products of this invention. The amount of carbon dioxide introduced into the beverage will depend upon the particular flavor system utilized and the amount of carbonation desired.

pH

The compositions of the present invention, particularly the beverage compositions, preferably have a pH of from about 2 to about 8, more preferably from about 2 to about 4.5, and most preferably from about 2.7 to about 4.2. Beverage acidity can be adjusted to and maintained within the requisite range by known and conventional methods, e.g., the use of food grade acid buffers. Typically, beverage acidity within the above recited ranges is a balance between maximum acidity for microbial inhibition and optimum acidity for the desired beverage flavor.

Organic as well as inorganic edible acids may be used to adjust the pH of the beverage composition. The acids can be present in their undissociated form or, alternatively, as their respective salts, for example, potassium or sodium hydrogen phosphate, potassium or sodium dihydrogen phosphate salts. The preferred acids are edible organic acids which include citric acid, malic acid, fumaric acid, adipic acid, phosphoric acid, gluconic acid, tartaric acid, ascorbic acid, acetic acid, phosphoric acid or mixtures thereof. The most preferred acids are citric and malic acids.

The acidulant can also serve as an antioxidant to stabilize beverage components. Examples of commonly used antioxidant include but are not limited to ascorbic acid, EDTA (ethylenediaminetetraacetic acid), and salts thereof.

This discussion of the composition uses, combinations, and benefits, is not intended to be limiting or all-inclusive. It is contemplated that other similar uses and benefits can be found that will fall within the spirit and scope of this invention.

Analytical Methods

As used herein, the term "hydrating mammalian skin" or the like means to enhance the moisture content of mammalian skin relative to moisture content wherein the user is not administrated a composition as described herein. Hydration of mammalian skin may be measured by any of a variety of methods well-known in the art, however, the preferred method is an in vivo method as set forth herein below. This method is referred to herein for simplicity as "the corneometer method." The corneometer method is performed as follows:

The corneometer method quantifies mammalian (preferably, human) skin hydration. The method is performed using the Courage and Khazaka Corneometer 820 PC. The method is based on the high degree of polarity of the water molecule. Because water exhibits the highest degree of polarity of any of the natural compounds found in the stratum corneum and epidermis, any measure of the electrical capacitance of the skin surface will be an indirect measurement of water presence and, therefore, mammalian skin surface hydration.

Thirty-two human female subjects are selected to determine mammalian skin hydration. Each subject should be from 35 to 55 years of age and in good general health. The subjects should refrain from using moisturizing products, soaps, or other cleansers on the test area for the duration of the study, including from first ingestion of a composition herein through skin hydration measurement.

On day 1 of the study, thirty-two human female subjects are randomly divided into two groups of sixteen human female subjects, denoted herein for simplicity as "Group 1" and "Group 2." Corneometer measurements are taken for each of the subjects. Skin surface hydration measurements are obtained from the volar forearm (test area) of each of the subjects. The Corneometer probe is wiped clean with a Kimwipe® and zeroed against a dry, clean surface, before each test site reading, to test the integrity of the system.

Subjects within Group 1 are then directed to ingest 500 mL of a composition as described herein once daily on days 1 through 3 of the study, and consume diets according to normal practice. Subjects within Group 2 do not ingest a composition as described herein, but consume diets according to normal practice on days 1 through 3 of the study.

On day 3, approximately four hours after ingestion of a composition herein (for Group 1 subjects) all thirty-two subjects report to a pre-determined testing location. Skin surface hydration measurements are obtained from the volar forearm (test area) of each of the subjects. Corneometer measurements are taken for each of the subjects. The Corneometer probe is wiped clean with a Kimwipe® and zeroed against a dry, clean surface, before each test site reading. For each subject, mammalian skin hydration measurements are baseline subtracted using, relative to each of the corresponding readings for such subject on day 1, to give a Corneometer reading for each subject. The Corneometer reading for all subjects in Group 1 are averaged. Similarly, the Corneometer reading for all subjects in Group 2 are averaged. The higher Corneometer reading among the two Groups indicates higher skin surface capacitance and therefore higher mammalian skin hydration. Following the procedures herein, Group 1 exhibits higher mammlian skin hydration, as attributed to ingestion of a composition herein. Visible effects may also be observed, for example, by expert skin graders.

Methods of Making

The present compositions are made according to methods which will be well known by the ordinarily skilled artisan. For convenience, non-limiting examples of methods of making follows.

To illustrate, the compositions of the present invention may be prepared by dissolving, dispersing, or otherwise mixing all components singularly or in suitable combinations together and in water where appropriate, agitating with a mechanical stirrer until all of the ingredients have been solubilized or adequately dispersed. Where appropriate, all separate solutions and dispersed may then be combined. When using tea extracts which typically are pH sensitive, it is important to adjust the desired pH with an acidulant and/or buffer system before adding the tea extracts to the mixture. Wherein a shelf stable composition is desired, the final mixture can optionally, but preferably, be pasteurized or filled aseptically at appropriate process conditions.

In making a ready-to-drink composition, a beverage concentrate may optionally be formed first. One method to prepare the concentrate form of the beverage composition would be to start with less than the required volume of water that is used in the preparation of the beverage composition. Another method would be to partially dehydrate the finally prepared beverage compositions to remove only a portion of the water and any other volatile liquids present. Dehydration may be accomplished in accordance with well known procedures, such as evaporation under vacuum. The concentrate can be in the form of a relatively thick liquid. A syrup is typically formed by adding suitable ingredients such as electrolytes or emulsions to the beverage concentrate. The syrup is then mixed with water to form a finished beverage or finished beverage concentrate.

Carbon dioxide can be introduced either into the water to be mixed with the beverage concentrate, or into the drinkable beverage composition, to achieve carbonation. The carbonated beverage composition can then be stored in a suitable container and then sealed. Techniques for making and carbonating beverage embodiments of the present invention are described in the following references: L. F. Green (ed.), *Developments in Soft Drinks Technology*, Vol. 1 (Elsevier, 1978); G. S. Cattell and P. M. Davies, "Preparation and Processing of Fruit Juices, Cordials and Drinks", *Journal of the Society of Dairy Technology*; Vol. 38 (1), pp. 21–27, A. H. Varnam and J. P. Sutherland, *Beverages—Technology, Chemistry and Microbiology*, Chapman Hall, 1994; and A. J. Mitchell (ed.), *Formulation and Production of Carbonated Soft Drinks*, Blackie and Sons Ltd., 1990.

Essentially dry mixtures of the present invention can be prepared by blending the proper amounts and ratios of all the required dry ingredients together. Alternatively, the finally prepared beverage compositions can be dehydrated to give the essentially dry mixture of the beverage composition. The essentially dry mixture, either as, for example, a powder, granules or tablets, can later be dissolved in a proper amount of water, carbonated or non-carbonated, to make the final drinkable beverage or taken in conjunction with water.

EXAMPLES

The following examples are illustrative of uses of the present compositions. Such examples are non-limiting illustrations and various modifications thereof may be made by one of ordinary skill in the art with the benefit of the present disclosure.

Example 1

A beverage composition is prepared by combining the following ingredients:

| Ingredient | Wt. % |
| --- | --- |
| Red Grape Extract (commercially available as Nutrifood ®, GNT International, Netherlands) | 2.00 |
| Apple Juice | 3.00 |
| Decaffeinated Green Tea Extract | 0.15 |
| Ginseng Extract (Panax) | 0.0125 |
| Glycerol | 4.00 |
| Aloe Vera Juice | 1.00 |
| Citric Acid | 0.10 |
| Sodium Citrate | 0.10 |
| Flavors | 0.5 |
| Aspartame | 0.004 |
| Acesulfame K | 0.009 |
| Ascorbic Acid | 40.0 (mg/100 g) |
| Vitamin E | 15 (mg/100 g) |
| Beta Carotene | 7.2 (mg/100 g) |
| Vitamin $B_6$ | 3.0 (mg/100 g) |
| Vitamin $B_1$ | 2.1 (mg/100 g) |
| Deionized Water | quantum satis |

Example 2

A beverage composition is prepared by blending the following ingredients:

| Ingredient | Wt % |
| --- | --- |
| Fruit Juice Single Strength | 10.00 |
| Decaffeinated Green Tea Extract | 0.20 |
| Aloe Gel | 1.50 |
| Glycerol | 4.50 |
| Sucrose | 7.00 |
| Citric Acid | 0.20 |
| Sodium Citrate | 0.10 |
| Flavors | 0.15 |
| Ginseng Extract (Panax) | 0.01 |
| Deionized Water | quantum satis |

Example 3

A beverage concentrate is prepared by blending the following ingredients:

| Ingredient | Wt % |
| --- | --- |
| Sugar | 25.0 |
| Glycerol | 15.0 |
| Decaffeinated Green Tea Extract | 0.80 |
| Red Grape Extract (commercially available as Nutrifood ®, GNT International, Netherlands) | 0.40 |
| Fructo-oligosaccahrides | 2.0 |
| Ascorbic Acid | 0.25 |
| Citric Acid | 0.75 |
| Sodium Citrate | 0.50 |
| Flavors | 0.80 |
| Aspartame | 0.025 |
| Acesulfame K | 0.060 |
| Deionized Water | quantum satis |

What is claimed is:

1. A method of hydrating mammalian skin comprising orally administering to a mammal in need thereof a substantially decaffeinated composition comprising:
    a) substantially decaffeinated green tea;
    b) one or more flavanols;
    c) at least two components selected from the group consisting of aloe, glycerol, and red grape extract; and
    d) from about 5% to about 99% water by weight of the composition; wherein the composition comprises less than about 0.005% caffeine by weight of the composition.

2. A method according to claim 1 wherein the composition comprises from about 0.0001% to about 1% of total flavanols by weight of the composition.

3. A method according to claim 2 wherein the composition comprises aloe, glycerol, and red grape extract.

4. A method according to claim 3 wherein the composition comprises from about 0.0001% to about 15% of the aloe by weight of the composition and from about 0.001% to about 20% of the glycerol by weight of the composition.

5. A method according to claim 4 wherein the composition comprises at least about 50% water by weight of the composition.

6. A method according to claim 5 wherein the composition comprises from about 0.004% to about 1% of the substantially decaffeinated green tea by weight of the composition.

7. A method according to claim 6 wherein the composition comprises from about 0.1% to about 5% of the aloe by weight of the composition and from about 2% to about 5% of the glycerol by weight of the composition.

8. A method according to claim 7 wherein the composition further comprises a nutrient.

9. A method according to claim 8 wherein the composition comprises from about 0.1% to about 5% of the red grape extract by weight of the composition.

10. A method according to claim 9 wherein at least one nutrient is selected from the group consisting of iron, zinc, calcium, niacin, thiamin, folic acid, iodine, vitamin A, vitamin C, vitamin $B_6$, vitamin $B_{12}$, vitamin D, vitamin E, and mixtures thereof.

11. A method according to claim 2 wherein at least one of the components is glycerol.

12. A method according to claim 11 wherein at least one of the components is aloe and wherein the composition comprises from about 0.0001% to about 15% of the aloe by weight of the composition and from about 0.001% to about 20% of the glycerol by weight of the composition.

13. A method according to claim 12 wherein the composition comprises at least about 50% water by weight of the composition.

14. A method according to claim 13 wherein the composition comprises from about 0.004% to about 1% of the substantially decaffeinated green tea by weight of the composition.

15. A method according to claim 14 wherein the composition comprises from about 0.1% to about 5% of the aloe by weight of the composition and from about 2% to about 5% of the glycerol by weight of the composition.

16. A method according to claim 15 wherein the composition further comprises a nutrient.

17. A method according to claim 16 wherein at least one nutrient is selected from the group consisting of iron, zinc, calcium, niacin, thiamin, folic acid, iodine, vitamin A, vitamin C, vitamin $B_6$, vitamin $B_{12}$, vitamin D, vitamin E, and mixtures thereof.

* * * * *